United States Patent [19]
Levy et al.

[11] Patent Number: 5,780,060
[45] Date of Patent: Jul. 14, 1998

US005780060A

[54] MICROCAPSULES WITH A WALL OF CROSSLINKED PLANT POLYPHENOLS AND COMPOSITIONS CONTAINING THEM

[75] Inventors: Marie-Christine Levy, Reims; Marie-Christine Andry, Dizy, both of France

[73] Assignee: Centre National de la Recherche Scientifique, Paris, France

[21] Appl. No.: 525,619

[22] PCT Filed: Feb. 1, 1995

[86] PCT No.: PCT/FR95/00116

§ 371 Date: Sep. 27, 1995

§ 102(e) Date: Sep. 27, 1995

[87] PCT Pub. No.: WO95/21018

PCT Pub. Date: Aug. 10, 1995

[30] Foreign Application Priority Data

Feb. 2, 1994 [FR] France .................................. 94 01146

[51] Int. Cl.$^6$ .............................. A61K 9/50; A61K 35/78
[52] U.S. Cl. ...................... 424/489; 424/195.1; 424/401; 424/451; 424/455; 424/499; 424/500; 424/501; 514/772.3; 514/773; 514/774; 514/775; 514/776; 514/777; 514/778; 514/779; 514/781; 514/782; 514/783; 514/801; 514/844; 514/952; 514/962; 264/4.32; 428/402.2

[58] Field of Search ....................... 424/489, 451, 424/499, 455, 401; 264/4.32; 428/402.2

[56] References Cited

U.S. PATENT DOCUMENTS 4,780,321  10/1988  Levy et al. ......................... 424/499

*Primary Examiner*—Thurman K. Page
*Assistant Examiner*—James M. Spear
*Attorney, Agent, or Firm*—Dennison, Meserole, Pollack & Scheiner

[57] ABSTRACT

Microcapsules based on crosslinked plant polyphenols are described. These microcapsules are obtained by the interfacial crosslinking of plant polyphenols, particularly flavonoids. When incorporated in a composition such as a cosmetic, pharmaceutical, dietetic or food composition, these microcapsules make it possible to prevent any impairment of this composition, in particular any color modification, while at the same time preserving the activity, especially the anti-free radical and/or antioxidizing activity, of the plant polyphenols, particularly the flavonoids.

35 Claims, No Drawings

MICROCAPSULES WITH A WALL OF CROSSLINKED PLANT POLYPHENOLS AND COMPOSITIONS CONTAINING THEM

This application is a 371 of PCT/FR 95/00116 filed Feb. 1, 1995.

Microcapsules with a wall of crosslinked plant polyphenols and compositions containing them The present invention relates essentially to the application, to plant polyphenols, of interfacial crosslinking by means of a crosslinking agent to form microcapsules, to the microcapsules produced in this way, to the processes for their manufacture and to the compositions containing the microcapsules obtained in this way, such as cosmetic, pharmaceutical, food and dietetic compositions.

Plant polyphenols constitute an important group of natural substances with well-known anti-free radical and antioxidizing properties (see for example: "Polyphenolic Phenomena", A. SCALBERT, Editor, INRA Editions, Paris, 1993). These compounds, including especially flavonoids such as, for example, procyanidolic oligomers or PCO, possess valuable biological properties associated in particular with their anti-free radical activity. For example, they are capable of preventing the harmful effects of free radicals on the skin and hence of playing a protective role against solar radiation and against ageing of the skin, and an anticarcinogenic role. They can also prevent erythema and couperose. Moreover, they possess properties which can be utilized in therapeutics, in particular in dermatology and for applications to the mucous membranes, such as antiinflammatory properties, vasculoprotective properties (treatment of ecchymoses, petechiae, gingivorrhagia, epistaxis, etc.) and antiallergic, antiulcer, antibacterial, antiviral and anticancer properties. Finally, when added to foods or dietetic products, they can preserve the preparations in which they are incorporated, by their antioxidizing action, and at the same time constitute a valuable supply of anti-free radical substances, making it possible to prevent diseases due to free radicals, such as cancer.

Thus they have applications especially in the fields of cosmetics, pharmaceutics, food and dietetics. However, it is often impossible to incorporate them into certain preparations, such as preparations for cosmetic or dermatological use for example, because of the dark coloration which these relatively unstable substances impart to said preparations.

Likewise, anthocyanin derivatives, which are colored polyphenolic substances also belonging to the flavonoid group (F. J. Francis, Crit. Rev. Food Sci. Nutri., 1989, 28, 273–314), also exhibit an anti-free radical activity and possess valuable biological properties, especially on the permeability and strength of the hair. However, they cannot generally be incorporated into certain preparations, such as preparations for cosmetic or dermatological use for example, because of their high tinctorial strength.

It is known that high-molecular polymers can be prepared by the interfacial polycondensation of a synthetic diphenol, namely bisphenol A, with diacid chlorides (W. M. Eareckson, J. Polymer Sci., 1959, 40, 399–406). On the basis of this principle, S. Suzuki et al. (Chem. Pharm. Bull., 1968, 6, 1629–1631) obtained microcapsules by applying the polycondensation reaction of bisphenol A with sebacoyl chloride to an emulsion.

However, no document in the prior literature describes the preparation of microcapsules by the interfacial crosslinking of plant polyphenols.

Within the framework of the invention, it has been discovered, unexpectedly, that the interfacial crosslinking of plant polyphenols, particularly flavonoids, by means of a crosslinking agent, preferably a diacid halide and particularly a diacid chloride, gives a product, especially microcapsules, which is particularly stable, notably in the presence of an aqueous medium, while at the same time preserving the initial activity of these plant polyphenols, in particular a biological activity and especially an anti-free radical activity, which is particularly remarkable.

Thus it has been observed, unexpectedly, that the interfacial acylation of phenolic groups of the plant polyphenol forms ester bonds and gives membranes of crosslinked polyphenol, while at the same time leaving a sufficient number of phenolic groups free to maintain the properties of the plant polyphenols, in particular their anti-free radical and antioxidizing properties.

It has also been observed that, when incorporated in a composition, this product avoids the risks of instability of this composition, especially as regards its coloration, said risks correlating with the presence, in this composition, of plant polyphenols, particularly flavonoids, which are liable to degrade.

Thus one main object of the present invention is to solve the new technical problem which consists in providing a solution for preparing a product from plant polyphenols, particularly flavonoids, which, when incorporated in a composition, does not impair its stability, in particular its color stability.

A further main object of the present invention is to provide a solution for preventing the diffusion of plant polyphenols, particularly flavonoids, especially in the dissolved state, into the whole of the composition in which they are incorporated.

Thus the present invention makes it possible to prevent any impairment, in particular any color modification over time, of a composition containing plant polyphenols, particularly flavonoids.

A further main object of the present invention is to provide a solution for preparing a product which does not stain the skin, from plant polyphenols, particularly flavonoids and especially anthocyanin derivatives, thereby enabling them to be incorporated in cosmetic or pharmaceutical preparations for application to the skin or the mucous membranes.

A further main object of the present invention is to solve the new technical problem which consists in providing a solution for preparing a product with good keeping qualities, in particular a stable color, from plant polyphenols, particularly flavonoids, thereby making it possible to prepare compositions for use in cosmetics or pharmaceutics, particularly dermatology, food or dietetics.

A further main object of the present invention is to solve the new technical problem which consists in providing a solution for preparing a stable form of plant polyphenols, particularly flavonoids, while at the same time preserving the specific initial activity of these plant polyphenols, particularly these flavonoids.

A further main object of the present invention is to solve the new technical problem which consists in providing a solution for preparing a stable product, particularly microcapsules, from plant polyphenols, particularly flavonoids, preserving the initial activity of these plant polyphenols, particularly these flavonoids, while at the same time making it possible, where appropriate, to encapsulate one or more active substances in the form of a solution, suspension or emulsion, thereby enabling the biological activity of this product or these microcapsules to be enhanced.

A further object of the present invention is to solve the abovementioned new technical problems by means of simple manufacturing processes which can be used on the industrial scale, in particular in the cosmetics, pharmaceuticals, food or dietetics industry. Preferably, this solution must make it possible to prepare microcapsules whose particle size can be adjusted at will, in particular over a range of dimensions from less than one micrometer to more than one millimeter.

Thus, according to the present invention, it has been discovered, totally unexpectedly, that microcapsules can be obtained by initiating a polycondensation reaction between a plant polyphenol and a crosslinking agent, preferably a diacid halide and particularly a diacid chloride, at the interface of the phases of an emulsion, in particular of the "water-in-oil" type. In this case, an aqueous solution of the plant polyphenol is first emulsified in a hydrophobic phase, after which a solution of crosslinking agent is added to the emulsion. Membranes consisting of crosslinked molecules of the plant polyphenol are then seen to form at the interface of the aqueous droplets as a result of the creation of ester bonds between the crosslinking agent and phenol groups of the plant polyphenol. After the reaction, these membranes therefore form microcapsules which can easily be separated from the reaction medium and washed to remove the plant polyphenol not bound to the membrane.

Furthermore, these microcapsules are sufficiently stable to undergo lyophilization without any destruction of their structure, and resume a spherical shape after rehydration, which constitutes another decisive technical advantage of the invention.

It has also been discovered that microcapsules can be obtained by initiating the polycondensation reaction in an emulsion of the "oil-in-water" type. In this case, a hydrophobic phase containing a crosslinking agent, preferably a diacid halide and particularly a diacid chloride, is emulsified in an aqueous phase containing the plant polyphenol, used as the continuous phase. The reaction is allowed to develop at the interface and agitation is maintained for a suitable time. A membrane is seen to form around the dispersed hydrophobic droplets, giving microcapsules with hydrophobic contents.

Thus, according to a first feature, the present invention covers microcapsules, characterized in that they comprise a wall formed of one or more plant polyphenols crosslinked in particular by means of interfacial crosslinking between the plant polyphenol or polyphenols and a crosslinking agent, preferably a diacid halide and particularly a diacid chloride.

In one advantageous embodiment, these microcapsules are characterized in that they comprise a protein, a polysaccharide, a polyalkylene glycol or any mixture of these substances. Advantageously, the wall of the microcapsules can also comprise a protein and/or a polysaccharide and/or a polyalkylene glycol co-cross-linked with the abovementioned plant polyphenol.

In one particularly advantageous embodiment, the abovementioned protein can possess a specific biological activity such as an enzymatic activity, examples being catalase, superoxide dismutase or glutathione peroxidase, in which case this activity can usefully add to the inherent activity of the plant polyphenol or polyphenols, particularly the flavonoid or flavonoids.

In another advantageous embodiment of the invention, the abovementioned microcapsules can be prepared from a single plant polyphenol or from mixtures of natural or unnatural origin containing plant polyphenols, for example fruit juices or extracts of plants or parts of plants.

In another particularly advantageous embodiment of the invention, the abovementioned plant polyphenols can be monocyclic or polycyclic plant polyphenols such as flavonoids, isoflavonoids, neoflavonoids, gallotannins and ellagotannins, catechol and derivatives thereof such as DL-3,4-dihydroxyphenylalanine or DL-DOPA, catecholamines such as 3-hydroxytyramine or dopamine, phloroglucinol, phenolic acids such as caffeic acid, dihydrocaffeic acid, protocatechuic acid, chlorogenic acid, isochlorogenic acid, gentisic acid, homogentisic acid, gallic acid, hexahydroxydiphenic acid, ellagic acid, rosmarinic acid or lithospermic acid, phenolic acid derivatives, particularly their esters or their heterosides, curcumin, polyhydroxylated coumarins, polyhydroxylated lignans or neolignans, or a mixture containing one or more plant polyphenols or derivatives thereof, such as silymarin. In particular, all the abovementioned polyphenols can be used in the form of preparations obtained from plants or parts of plants, such as extracts, tinctures, fruit juices or wines.

The particularly advantageous plant polyphenols within the framework of the invention are those which are extracted especially from plants belonging to the following genera: Gingko, Lespedeza, Passiflora, Silybum, Citrus, Hamamelis, Thymus, Chamaemelum, Achillea, Equisetum, Sophora, Fagopyrum, Eucalyptus, Sambucus, Betula, Vitis, Pinus, Crataegus, Quercus, Ratanhia, Lythrum, Acacia, Cupressus, Vaccinium, Ribes, Centaurea, Rosa, Hibiscus, Malva, Podophyllum, Schizandra, Gaiacum, Arctostaphylos, Cynara, Rosmarinus, Orthosiphon, Solidago, Lithospermum, Curcuma, Aesculus, Melilotus, Ammi, Hieracium, Angelica, Asperula.

In one advantageous variant, the abovementioned plant polyphenols are flavonoids selected from the group consisting of a flavone such as apigenol or luteolol, a flavonol such as quercetin or kaempferol, a flavone or flavonol heteroside such as rutin and derivatives thereof, a flavanone such as flavanone, naringenin or hesperetin, a flavanone heteroside such as naringin, hesperidin or diosmin, a flavanone derivative such as diosmoside, a biflavonoid, a flavone or flavanone dimer such as amentoflavone, a chalcone such as isoliquirtigenin or hesperidin methylchalcone, a flavanonol such as taxifoliol or a substance derived from taxifoliol, like silybin, silychristin or silydianin, a flavan-3-ol such as (+)-catechol or (−)-epicatechol, a polymer formed of flavan-3-ol basic structural units, which is generally known by the name of "proanthocyanidine" or by the expression "condensed tannin", in particular an oligomer comprising from 2 to 8 of these units, which is generally called a "procyanidolic oligomer" (PCO), or an anthocyanoside such as malvoside, or a mixture containing one or more flavonoids, particularly in the form of extracts of fruits or extracts of plants or parts of plants.

In particular, the abovementioned mixture of flavonoids is preferably selected from the group consisting of mixtures of citroflavonoids extracted from various Citrus (Rutaceae), a mixture of flavonoids extracted from *Silybum marianum* (Compositae), or silymarin, extracts of *Gingko biloba* (Gingkoaceae), anthocyanoside-rich extracts of blueberry, blackcurrant fruits, grape skins or red vine leaf, fruit juices such as grape or blackcurrant juices, as such, concentrated or dehydrated, especially by atomization or lyophilization, red wines, as such, concentrated or dehydrated, or various mixtures thereof.

In another advantageous embodiment of the invention, the abovementioned protein can be selected from the group consisting of albumins such as serum albumin, ovalbumin or alpha-lactalbumin, globulins, fibrinogen, casein, vegetable proteins such as soya proteins, glutelins which will preferably have been degraded, solubilized scleroproteins, collagen, atelocollagen, gelatin, gelatin hydrolyzates, peptones, hemoglobin, enzymes such as catalase, superoxide dismutase or glutathione peroxidase, mixtures containing hydrophilic proteins, such as whole milk or totally or partially skimmed milk, powdered milk or condensed milk, whey proteins, soya flour and mixtures of atelocollagen and glycosaminoglycans.

In another advantageous embodiment of the invention, the abovementioned polysaccharide can be selected from the group consisting of dextrans, alginic acid and water-soluble salts thereof, particularly sodium alginate, vegetable gums, carrageenans, pectins, soluble starch derivatives, soluble cellulose derivatives and glycosaminoglycans.

In another advantageous embodiment of the invention, the polyalkylene glycol can be selected from the group consisting of polyethylene glycols and polypropylene glycols.

In yet another advantageous embodiment of the invention, the abovementioned microcapsules are prepared by the interfacial crosslinking of an emulsion whose aqueous phase contains from 1% to 40% and preferably between 1 and 20% by weight of plant polyphenols, based on the total weight of the aqueous phase. If one of the abovementioned proteins and/or polysaccharides and/or polyalkylene glycols is present, the total concentration of this or these substances in the aqueous phase is advantageously between 0.1 and 30% by weight and preferably between 1 and 10% by weight, based on the total weight of the aqueous phase.

In yet another advantageous embodiment of the invention, the abovementioned microcapsules are prepared by the interfacial crosslinking of an emulsion whose disperse phase to be encapsulated contains one or more water-soluble, liposoluble or insoluble active substances incorporated in the form of a solution, suspension or emulsion, in particular a preferably insoluble mineral substance which reflects solar radiation, a vegetable oil or an oily solution containing a lipophilic active substance such as a liposoluble sun filter. The microcapsules obtained thus contain said water-soluble, liposoluble or insoluble substances.

In one particularly advantageous embodiment, the active substances incorporated in the microcapsules according to the invention can be selected from the group consisting of a mineral substance which reflects solar radiation, such as an iron oxide, titanium oxide, zinc oxide, talc or kaolin, a vegetable oil such as a cereal germ oil, a deodorized fish liver oil, or an oily solution of a liposoluble substance such as vitamin A, vitamin D2, vitamin E or tocopherol, an essential fatty acid such as linoleic acid, linolenic acid or arachidonic acid, a ceramide, a liposoluble ascorbic acid derivative such as ascorbyl palmitate, or a liposoluble sun filter such as a cinnamic acid ester, a paraaminobenzoic acid ester, a salicylic acid ester, a benzophenone, benzylidenecamphor and derivatives thereof, a dibenzoylmethane derivative, a benzimidazole or a photoactive substance such as bergapten or any other psoralen derivative, or else a mixture containing several active substances.

According to a second feature, the present invention also covers a process for the manufacture of the microcapsules as defined above, characterized in that an emulsion of the water-in-oil type is subjected to interfacial crosslinking comprising the following essential steps:

a) an aqueous phase is prepared which contains the plant polyphenol or the mixture of plant polyphenols to be crosslinked, b) a hydrophobic phase is prepared which contains one or more surfactants, if appropriate, c) said aqueous phase is emulsified in the abovementioned hydrophobic phase so that the hydrophobic phase forms the continuous phase in which the aqueous phase forms the disperse phase, d) the crosslinking agent, dissolved in a liquid miscible with the hydrophobic phase, is added to the resulting emulsion, with agitation, in order to effect interfacial crosslinking of the crosslinking agent and the plant polyphenol or polyphenols contained in the aqueous phase, e) agitation is maintained for a suitable reaction time to allow sufficient crosslinking, resulting in the formation of microcapsules whose wall comprises the plant polyphenol or polyphenols crosslinked by the crosslinking agent, and f) the microcapsules thus formed are collected by any appropriate means.

According to a third feature, the present invention also covers a process for the manufacture of the microcapsules defined above, characterized in that an emulsion of the oil-in-water type is subjected to interfacial crosslinking comprising the following essential steps:

a) a hydrophobic phase is prepared in which the crosslinking agent is dissolved, b) an aqueous phase is prepared which contains the plant polyphenol or the mixture of plant polyphenols to be crosslinked and, if appropriate, one or more surfactants, c) the hydrophobic phase is emulsified in the abovementioned aqueous phase so that the aqueous phase forms the continuous phase in which the hydrophobic phase forms the disperse phase, d) the whole is agitated for a suitable reaction time to allow sufficient crosslinking, resulting in the formation of microcapsules whose wall comprises the plant polyphenol or polyphenols crosslinked by the crosslinking agent, and e) the microcapsules thus formed are collected by any appropriate means.

The emulsification step of one or other of the processes of the above two features is carried out by using one of the techniques well known to those skilled in the art, especially by varying the respective proportions of the aqueous phase and the hydrophobic phase, and/or by using one or more appropriate surfactants dispersed in the hydrophobic phase and/or in the aqueous phase.

An emulsion of the water-in-oil type will preferably be obtained by using one or more surfactants selected in particular from sorbitan esters, such as Span 85®, fatty acid esters of glycerol, such as glycerol monooleate, and fatty acid esters of glycols, such as ethylene glycol stearate.

An emulsion of the oil-in-water type will preferably be obtained by using one or more surfactants selected for example from polyethoxylated fatty acid esters of sorbitan, or Tween®, particularly Tween 20®. It should be noted, however, that the presence of a surfactant is not critical within the framework of the processes according to the invention.

This emulsification step is carried out with agitation by any appropriate means, in particular by mechanical agitation or by means of ultrasound, or else by means of a high-pressure homogenizer, for example a commercially available homogenizer operating at up to 700 bar. The use of a high-pressure homogenizer is especially advantageous when it is desired to obtain particularly fine droplets.

In general, it is necessary to wash the microcapsules obtained after crosslinking in order to remove the excess crosslinking agent and the plant polyphenol or polyphenols which have not reacted or are not encapsulated in the microcapsules. To perform this operation, the microcapsules are separated from the reaction medium by centrifugation, decantation or any other appropriate means. In the case of the process comprising water-in-oil emulsification, the microcapsules are washed by successive resuspension in a hydrophobic liquid such as one of the liquids used to form the hydrophobic phase of the initial emulsion, then in an alcohol such as ethanol or methanol, either pure or diluted with water, and then in water. In the case of the process comprising oil-in-water emulsification, the microcapsules are washed in water or in an appropriate aqueous solution.

In one variant of one or other of the processes of the above features, a protein and/or a polysaccharide and/or a polyalkylene glycol is added to the aqueous phase during its preparation, it being possible for the wall of the microcapsules formed by the crosslinking reaction to comprise the plant polyphenol or polyphenols co-crosslinked with said protein and/or said polysaccharide and/or said polyalkylene glycol by the crosslinking agent.

The incorporation of polyalkylene glycols, particularly a polyethylene glycol, into the aqueous phase of the microcapsules makes it possible to increase the hydrophilicity of these microcapsules, especially in the case where the polyphenolic product used to prepare the microcapsules is of a relatively hydrophobic nature. This hydrophilicity can be adjusted by increasing the proportion of polyalkylene glycol incorporated. Thus, when placed in aqueous media, these microcapsules rapidly resume a spherical shape and give very readily dispersible sediments. In addition, exchanges between the interior and exterior of the microcapsules will be facilitated, which in particular may enable constituents of the external medium to come into contact more easily with functional groups carried by the internal face of the membrane, thereby increasing the activity of the microcapsules. Furthermore, the presence of a polyalkylene glycol, particularly a polyethylene glycol, in the microcapsules can improve the retention of encapsulated water-soluble molecules.

In one advantageous embodiment of these processes, the crosslinking agent comprises a diacid halide, particularly a diacid chloride, which is preferably selected from the group consisting of an aliphatic or aromatic diacid chloride such as sebacoyl chloride, succinyl chloride, adipoyl chloride, terephthaloyl chloride or glutaryl chloride. The concentration of diacid halide will preferably be between 0.2% and 10% by weight of the total weight of the reaction medium.

Furthermore, the reaction time can naturally vary according to the reactants used and especially according to the nature of the diacid halide, particularly the diacid chloride. The reaction time will generally be between 5 min and 2 h and advantageously between 15 and 60 min.

Also, the pH of the reaction is advantageously between 8 and 14 and preferably between 9 and 12. This reaction pH can be assured by using buffer solutions or solutions of an alkaline agent such as sodium hydroxide or potassium hydroxide.

Liquid substances well known to those skilled in the art may be used as substances for forming the hydrophobic phase.

The currently preferred hydrophobic liquid substances are selected from the group consisting of halogenated or non-halogenated hydrocarbons such as cyclohexane, chloroform or dichloromethane, fatty acid esters such as isopropyl myristate or ethyl oleate, commercially available mixtures of fatty acid esters such as, for example, the product Dragoxat® marketed by the firm DRAGOCO, vegetable oils such as olive oil, sweet-almond oil or groundnut oil, mineral oils such as a paraffin oil, and any mixture of these hydrophobic liquid substances.

In one variant of any one of the abovementioned processes, one or more active substances, in the form of a solution, suspension or emulsion, in particular a preferably insoluble mineral substance which reflects solar radiation, an oil or an oily solution of a liposoluble substance such as a liposoluble sun filter, are incorporated into the phase to be dispersed, which forms the liquid phase to be encapsulated.

Thus the process according to the invention enables the size of the microparticles to be adjusted at will, in particular over a range of dimensions from less than one micrometer to more than one millimeter. The diameter of the microcapsules according to the invention is generally situated in the range between 0.1 µm (micrometer) and 3 mm.

In yet another advantageous embodiment of the invention, the microcapsules with a wall of crosslinked plant polyphenols according to the present invention can be used in the as-manufactured state, i.e. fresh. In this case, they contain aqueous or hydrophobic disperse phase, facilitating their incorporation into hydrophilic or, respectively, hydrophobic vehicles.

Again, in one advantageous embodiment of the invention, the abovementioned microcapsules can take the form of an aqueous suspension whose concentration can be adjusted and which can be incorporated directly into formulations containing a hydrophilic vehicle.

In another advantageous embodiment of the invention, the microcapsules with a wall of crosslinked plant polyphenols according to the present invention can be in dehydrated form, produced especially by lyophilization, this being an easy and reliable means of storage.

Thus, in one advantageous embodiment, the abovementioned microcapsules take the form of a lyophilized powder. Within the framework of the invention, the microcapsules with a wall of crosslinked polyphenols easily resume a spherical shape after rehydration, while at the same time preserving their initial activity.

According to a fourth feature, the present invention also covers compositions, particularly cosmetic or pharmaceutical compositions, especially dermatological compositions, dietetic compositions or food compositions, characterized in that they comprise microcapsules with a wall of crosslinked plant polyphenols, as defined above.

In one advantageous embodiment, the concentration of microcapsules of plant polyphenols according to the invention will be between 0.01 and 10% by weight of the total weight of the final composition and preferably between 0.1 and 5% by weight of the final composition.

As stated previously, the microcapsules of the invention with a wall of crosslinked plant polyphenols preserve the initial activity of the plant polyphenols. Consequently, they are particularly useful as free radical scavengers by virtue of their anti-free radical activity. Thus these microcapsules are advantageously used in cosmetic or pharmaceutical compositions, especially dermatological compositions, for preventing ageing of the skin, especially actinic ageing.

Thus, according to a fifth feature, the present invention also covers a cosmetic or pharmaceutical method, especially a dermatological method, of treating a human in order to prevent ageing of the skin, especially the actinic ageing generally due to free radicals, characterized in that an effective amount of microcapsules with a wall of crosslinked plant polyphenols according to the invention, optionally included in a cosmetically or pharmaceutically acceptable excipient, vehicle or carrier, is applied to the areas of the skin or hair which are sensitive to the action of free radicals, especially the free radicals resulting from actinic exposure. In this treatment, the concentration of microcapsules will normally be between 0.01 and 10% by weight and preferably between 0.1 and 5% by weight of the composition containing the microcapsules.

Of course, these compositions can take a variety of forms acceptable in cosmetics, pharmaceutics, food or dietetics. These forms are well known to those skilled in the art. Non-limiting examples which may be mentioned are creams, ointments, lotions, especially hair lotions, gels, milks, suspensions, powders and gelatin capsules.

Finally, according to a sixth feature, the present invention also covers a process for the preparation of a composition incorporating one or more plant polyphenols, characterized in that, in order to prevent any impairment, especially any color modification of the composition over time, while at the same time preserving the activity of the plant polyphenols, especially the anti-free radical and/or antioxidizing and/or biological activity, said polyphenols are incorporated into said composition in the form of microcapsules as defined above or obtained by carrying out one of the processes described above.

It should be noted that the different variants have not been repeated within the framework of one or other of the above features, but it is quite clear that the invention covers, independently and for each of the features, each and every one of the variants which have been described above or will be described in the remainder of the description for one or other of the features of the invention.

Other objects, characteristics and advantages of the invention will become clearly apparent from the following explanatory description referring to various Examples of the invention, which are given simply by way of illustration and cannot therefore in any way limit the scope of the invention. All the percentages are given by weight in the Examples, unless indicated otherwise.

EXAMPLE 1

Manufacture of Microcapsules Consisting of Pine Bark Procyanidolic Oligomers (PB PCO) Crosslinked with Terephthaloyl Chloride (TC)

a) Preparation of the aqueous phase 300 mg of PB PCO (SARPAP) are dissolved in 3 ml of a carbonate buffer of pH 11.

b) Emulsification 3 ml of this solution are emulsified, by agitation at 3000 rpm, in 15 ml of cyclohexane to which 5% of Span 85® has been added.

c) Addition of the crosslinking agent

After 5 min, 20 ml of a 5% (w/v) solution of TC (Janssen Chimica) in a 1:4 (v/v) chloroform/cyclohexane mixture are added to the emulsion and agitation is maintained for 30 min.

d) Washing

The microcapsules are separated off by centrifugation and washed by successive resuspension in cyclohexane, in 95% ethanol to which 2% of Tween 20® has been added, in 95% alcohol and finally in distilled water.

A beige sediment of microcapsules is obtained. Examination by optical microscopy shows attractive, round, transparent, very independent microcapsules with a size of 5 to 20 µm. The microcapsules are intact after lyophilization. Examination by scanning electron microscopy shows clearly distinct particles with a continuous membrane. Stability: In the form of an aqueous suspension, the microparticles can be stored for at least 7 months at +4° C., at least 3½ months at 20° C. and at least 3½ months at +45° C.: the microcapsules are intact, their color is unmodified and the supernatant is colorless.

Anti-free radical activity of the lyophilized microcapsules:

The anti-free radical activity was measured in accordance with the activity test described in Example 37.

The result of this test is expressed as the percentage scavenging of the free radicals relative to a control sample not containing a free radical scavenger. Furthermore, the preservation of the anti-free radical activity, i.e. the free radical scavenging activity, was also measured by comparison with non-crosslinked flavonoids, namely grape seed procyanidolic oligomers (GS PCO) in this instance.

The results are given in Table II at the end of the description. It is pointed out here that the antifree radical activity of the microcapsules of this Example, according to the invention, is 81±4%, which is essentially similar to the anti-free radical activity of GS PCO of 91±2%; this demonstrates that the initial activity of the flavonoids is preserved, despite crosslinking.

EXAMPLE 2

Manufacture of Microcapsules Consisting of Pine Bark Procyanidolic Oligomers (PB PCO) Crosslinked with Terephthaloyl Chloride (TC)

a) Preparation of the aqueous phase 300 mg of PB PCO (SARPAP) are dissolved in 3 ml of a carbonate buffer of pH 9.8.

b) Emulsification 3 ml of this solution are emulsified, by agitation at 3000 rpm, in 15 ml of cyclohexane to which 5% of Span 85® has been added.

c) Addition of the crosslinking agent

After 5 min, 20 ml of a 2.5% (w/v) solution of TC (Janssen Chimica) in a 1:4 (v/v) chloroform/cyclohexane mixture are added to the emulsion and agitation is maintained for 30 min.

This gives a buff-colored sediment formed of transparent microcapsules with a mean diameter of 30 µm. The microcapsules are intact after storage for one year as an aqueous suspension at 20° C. Their color has not changed and the supernatant is perfectly colorless.

EXAMPLE 3

Manufacture of Microcapsules Consisting of Pine Bark Procyanidolic Oligomers (PB PCO) and Bovine Serum Albumin (BSA) Co-crosslinked with Terephthaloyl Chloride (TC)

The protocol described in Example 1 is applied using as the aqueous phase a solution containing 10% of PB PCO and 5% of BSA (Fraction V, Sigma) in the buffer of pH 11.

This gives a beige sediment formed of attractive independent microcapsules with a diameter of 5–10 µm.

Stability: In the form of an aqueous suspension, the microparticles can be stored for at least 7 months at +4° C., at least 1 month at 20° C. and at least 3 weeks at +45° C.: the microcapsules are intact, their color is unmodified and the supernatant is colorless.

Results of the determination of anti-free radical activity on lyophilized microcapsules: the scavenging is 51±1% (see Table II).

EXAMPLE 4

Manufacture of Microcapsules Consisting of Pine Bark Procyanidolic Oligomers (PB PCO) and Ovalbumin Crosslinked with Terephthaloyl Chloride (TC)

The protocol described in Example 1 is applied using as the aqueous phase a solution containing 10% of PB PCO and 5% of ovalbumin (Sigma) in the carbonate buffer of pH 11.

This gives a sediment formed of microcapsules with a diameter of 10–80 µm.

EXAMPLE 5

Manufacture of Microcapsules Consisting of Grape Seed Procyanidolic Oligomers (GS PCO) Crosslinked with Terephthaloyl Chloride (TC)

The protocol described in Example 1 is applied using as the aqueous phase a 10% solution of grape seed procyanidolic oligomers (GS PCO, SARPAP) in the buffer of pH 11.

This gives a buff-colored sediment formed of attractive, spherical, transparent microcapsules with a diameter of 5–25 µm. Examination by scanning electron microscopy shows independent particles with a continuous membrane.
Stability: In the form of an aqueous suspension, the microparticles can be stored for at least 6 months at +4° C., at least 1 month at 20° C. and at least 3 weeks at +45° C.: the microcapsules are intact, their color is unmodified and the supernatant is colorless.
Results of the determination of anti-free radical activity on lyophilized microcapsules: the scavenging is 71±2% (see Table II).

EXAMPLE 6

Manufacture of Microcapsules Consisting of Grape Seed Procyanidolic Oligomers (GS PCO) and Whey Proteins Co-crosslinked with Terephthaloyl Chloride (TC)

The protocol described in Example 1 is applied using as the aqueous phase a solution containing 10% of grape seed procyanidolic oligomers (GS PCO, SARPAP) and 5% of a whey protein concentrate (Prosobel S65E, Bel Industries) in the buffer of pH 11.

This gives a bulky light brown sediment of spherical microcapsules with a diameter of 5–20 µm. Examination by scanning electron microscopy shows independent particles with a continuous membrane. Stability: In the form of an aqueous suspension, the microparticles can be stored for at least 7 months at +4° C., at least 1 month at 20° C. and at least 3 weeks at +45° C.: the microcapsules are intact, their color is unmodified and the supernatant is colorless.

Anti-free radical activity of the lyophilized microcapsules: the scavenging is 83±1% (see Table II).

EXAMPLE 7

Manufacture of Microcapsules Consisting of Grape Seed Procyanidolic Oligomers (GS PCO) Crosslinked with Sebacoyl Chloride (SC)

a) Preparation of the aqueous phase 300 mg of GS PCO (SARPAP) are dissolved in 3 ml of 2M sodium hydroxide.

b) Emulsification 3 ml of this solution are emulsified, by agitation at 3000 rpm, in 15 ml of cyclohexane to which 5% of Span 85® has been added.

c) Addition of the crosslinking agent

After 5 min, 20 ml of a 5% (v/v) solution of SC (SIGMA) in a 1:4 (v/v) chloroform/cyclohexane mixture are added to the emulsion and agitation is maintained for 30 min.

d) Washing

The washes are effected as described in Example 1.

This gives microcapsules with a size of 5–15 µm. Examination by scanning electron microscopy shows independent particles with a continuous membrane.

EXAMPLE 8

Manufacture of Microcapsules Consisting of Grape Seed Procyanidolic Oligomers (GS PCO) and Whey Proteins Co-crosslinked with Sebacoyl Chloride (SC)

The protocol described in Example 7 is reproduced using as the aqueous phase a solution containing 10% of GS PCO and 5% of a whey protein concentrate (Prosobel S65E, Bel Industries) in 2M sodium hydroxide.

This gives a bulky sediment formed of attractive microcapsules with a diameter of 10–20 µm.

EXAMPLE 9

Manufacture of Microcapsules Consisting of Catechol Crosslinked with Terephthaloyl Chloride (TC)

The protocol described in Example 1 is applied using as the aqueous phase a 10% solution of catechol ((+)-catechol, SIGMA) in 2M sodium hydroxide.

This gives an ochre sediment of attractive microcapsules with a diameter of 5–15 µm.
Stability: In the form of an aqueous suspension, the microparticles can be stored for at least 1 month at 20° C. and at least 3 weeks at +45° C.: the microcapsules are intact, their color is unmodified and the supernatant is colorless.
Anti-free radical activity of the lyophilized microcapsules: the scavenging is 79±3% (see Table II).

EXAMPLE 10

Manufacture of Microcapsules Consisting of Catechol and Ovalbumin Co-crosslinked with Terephthaloyl Chloride (TC)

The protocol described in Example 1 is applied using as the aqueous phase a solution containing 10% of catechol and 2% of ovalbumin (SIGMA) in 2M sodium hydroxide.

This gives a sediment of independent microcapsules with a diameter of 10–20 µm.

EXAMPLE 11

Manufacture of Microcapsules Consisting of Catechol and Whey Proteins Co-crosslinked with Terephthaloyl Chloride

The protocol described in Example 1 is applied using as the aqueous phase a solution containing 10% of catechol and 3% of a whey protein concentrate (Prosobel S65E, Bel Industries) in 2M sodium hydroxide.

This gives a bulky yellow sediment formed of attractive microcapsules with a diameter of 5–20 µm.
Stability: In the form of an aqueous suspension, the microparticles can be stored for at least 1 month at 20° C. and at least 3 weeks at +45° C.: the microcapsules are intact, their color is unmodified and the supernatant is colorless.
Results of the determination of anti-free radical activity on lyophilized microcapsules: the scavenging is 64±5%.

EXAMPLE 12

Manufacture of Microcapsules Consisting of Catechol Crosslinked with Sebacoyl Chloride (SC)

The protocol described in Example 7 is reproduced using as the aqueous phase a solution containing 10% of catechol in 2M sodium hydroxide.

This gives microcapsules with a diameter of 5–25 µm.

EXAMPLE 13

Manufacture of Microcapsules Consisting of Catechol and Ovalbumin Co-crosslinked with Sebacoyl Chloride (SC)

The protocol described in Example 7 is applied using as the aqueous phase a solution containing 10% of catechol and 2% of ovalbumin in 2M sodium hydroxide.

This gives a bulky sediment formed of attractive microcapsules with a diameter of 5–20 µm.

EXAMPLE 14

Manufacture of Microcapsules Consisting of Catechol and Milk Proteins Co-crosslinked with Sebacoyl Chloride (SC)

Preparation of the aqueous phase:

4 ml of milk (Viva, CANDIA) are mixed with 2 ml of 6M sodium hydroxide. Catechol is dissolved in this solution at a concentration of 10%.

3 ml of the solution obtained are used for emulsification under the conditions described in Example 7. Crosslinking and washing are then carried out as described in Example 7.

This gives a bulky sediment formed of attractive microcapsules with a diameter of 5–25 µm.

EXAMPLE 15

Manufacture of Microcapsules Consisting of Grape Seed Procyanidolic Oligomers (GS PCO) Crosslinked with Terephthaloyl Chloride (TC)

The protocol described in Example 1 is applied using as the aqueous phase a 10% solution of grape seed procyanidolic oligomers (Leucocianidine, INDENA) in the buffer of pH 11 and an agitation speed of 5000 rpm. The microcapsules are washed successively in cyclohexane, in 95% ethanol to which 2% of Tween 20® has been added, in methanol and finally in distilled water.

This gives a buff-colored sediment formed of attractive, spherical, transparent microcapsules. The mean diameter, determined with the aid of a Coulter LS 100 granulometer (Coultronics), is 6.57 µm ±0.25.

Stability: In the form of an aqueous suspension, the microparticles can be stored for at least 5 months at 4° C., at 20° C. and at 45° C. The microcapsules are intact, their color is unmodified and the supernatant is colorless.

Determination of the anti-free radical activity on fresh microcapsules suspended in distilled water (concentration of about 0.7% by dry weight of microcapsules): see Table II.

EXAMPLE 16

Manufacture of Microcapsules Consisting of Grape Seed Procyanidolic Oligomers (GS PCO) and Dextran Co-crosslinked with Terephthaloyl Chloride (TC)

The protocol described in Example 15 is applied using as the aqueous phase a solution containing 10% of GS PCO (Leucocianidine, INDENA) and 5% of dextran (average mol. 41,600, Sigma) in the buffer of pH 11.

This gives a buff-colored sediment formed of attractive, independent, transparent, thick-walled microcapsules with a diameter of 5–15 µm. As an aqueous suspension, these microcapsules can be stored for at least 6 weeks at 20° C. The supernatant remains colorless.

EXAMPLE 17

Manufacture of Microcapsules from Dry Blueberry Extract and Terephthaloyl Chloride (TC)

A dry aqueous-alcoholic blueberry extract is used which contains anthocyanosides in an amount corresponding to 15% of anthocyanidines (INDENA).

The protocol described in Example 1 is applied using as the aqueous phase a 10% solution of this extract in the buffer of pH 11.

This gives a purplish-red sediment formed of attractive transparent microcapsules with a diameter of 2 to 15 µm and with a clearly visible membrane. The microcapsules are very readily resuspended in water to give a suspension of uniform color. This does not leave a stain when applied to the skin. After sedimentation, the suspension leaves a colorless supernatant. The same applies after storage for 15 days at 20° C. or at 45° C.

EXAMPLE 18

Manufacture of Microcapsules from Red Grape Juice and Terephthaloyl Chloride (TC)

1 ml of the buffer of pH 11 is added to 2 ml of grape juice ("Raisin rouge, pur jus", BONNETERRE).

The protocol described in Example 1 is applied using this mixture as the aqueous phase and using an agitation speed of 5000 rpm.

This gives an off-white sediment formed of thin-walled microcapsules with a diameter of 1 to 4 µm.

EXAMPLE 19

Manufacture of Microcapsules from Red Grape Juice Lyophilizate and Terephthaloyl Chloride (TC)

A lyophilizate of grape juice ("Raisin rouge, pur jus", BONNETERRE) is prepared. A 15% solution of this lyophilizate in the buffer of pH 11 is then prepared.

The protocol described in Example 1 is applied using this mixture as the aqueous phase.

This gives a beige sediment formed of attractive transparent microcapsules with a clearly visible membrane and with a diameter of 10 to 30 µm.

EXAMPLE 20

Manufacture of Microcapsules from Blackcurrant Juice and Terephthaloyl Chloride (TC)

1 ml of the buffer of pH 11 is added to 2 ml of blackcurrant juice ("Nectar de cassis", EDEN).

The protocol described in Example 1 is applied using this mixture as the aqueous phase and using an agitation speed of 5000 rpm.

This gives a pale pink sediment formed of thin-walled microcapsules with a diameter of 2 to 5 µm.

EXAMPLE 21

Manufacture of Microcapsules from Red Wine and Terephthaloyl Chloride (TC)

1 ml of the buffer of pH 11 is added to 2 ml of red wine (Bordeaux: Chateau Grave de Blanquet, 1989).

The protocol described in Example 1 is then reproduced using this mixture as the aqueous phase and using an agitation speed of 5000 rpm.

This gives a pale pink residue formed of very small microcapsules with a diameter of 1 to 3 µm.

EXAMPLE 22

Manufacture of Microcapsules from Powdered Grape Skin Extract and Terephthaloyl Chloride (TC)

A 10% solution of a powdered grape skin extract ("Biocon grape skin extract powder", QUEST International) in the buffer of pH 11 is prepared.

The protocol described in Example 1 is applied using this mixture as the aqueous phase and a 2.5% solution of TC.

This gives a plum-colored residue formed of microcapsules with a diameter of 5–30 µm. These microcapsules disperse readily in water to give a homogeneous purplish-red suspension which does not stain the skin. After sedimentation, the suspension leaves a colorless supernatant.

After one month at 4° C. or at 45° C., the supernatant of the aqueous suspension of microcapsules is still colorless and the residue of microcapsules is still plum-colored.

EXAMPLE 23

Manufacture of Microcapsules from Dry Blueberry Extract, Procyanidolic Oligomers and Terephthaloyl Chloride (TC)

A dry aqueous-alcoholic blueberry extract is used which contains anthocyanosides in an amount corresponding to 15% of anthocyanidines (INDENA).

A solution containing 10% of this extract and 5% of GS PCO (Leucocianidine, INDENA) in the buffer of pH 11 is prepared.

The protocol described in Example 1 is applied using this solution as the aqueous phase.

This gives a residue of raspberry-red micro-capsules with a diameter of 5 to 15 µm which disperse readily in water to give a suspension of homogeneous color. After sedimentation, the supernatant is colorless.

EXAMPLE 24

Manufacture of Microcapsules Consisting of Grape Seed Procyanidolic Oligomers (GS PCO) Crosslinked with Terephthaloyl Chloride (TC), and Containing an Oil A 10% solution of GS PCO (SARPAP) in the buffer of pH 11 is prepared. 2 ml of olive oil are emulsified in 12 ml of this solution by agitation for 2 min at 5000 rpm.

The agitation speed is then reduced to 3000 rpm and 60 ml of cyclohexane containing 5% of Span 85® are added.

After agitation for 3 min, 80 ml of a 5% (w/v) solution of TC in a 1:4 (v/v) chloroform/cyclohexane mixture are added to the emulsion and agitation is maintained for 30 min.

The reaction medium is diluted by the addition of 50 ml of cyclohexane and the microcapsules are then separated off by centrifugation and washed by successive resuspension in cyclohexane, in water to which 2% of Tween 20® has been added, and finally in distilled water.

This gives buff-colored microcapsules floating on the surface of the water. Microscopic examination shows spherical vesicles containing bright refringent droplets.

EXAMPLE 25

Manufacture of Microcapsules from Procyanidolic Oligomers, Catalase and Terephthaloyl Chloride (TC)

A solution containing 10% of GS PCO (Leucocianidine, INDENA) and 3% of catalase (from bovine liver, C-10, SIGMA) in the buffer of pH 11 is prepared.

The protocol described in Example 1 is applied using this solution as the aqueous phase.

This gives attractive buff-colored microcapsules with a diameter of 10–30 µm.

If a small amount of freshly prepared microcapsules is removed with a spatula and brought into contact with 110 volume hydrogen peroxide, a copious foam is immediately observed, showing that the catalase contained in the microcapsules preserves an enzymatic activity.

EXAMPLE 26

Manufacture of Microcapsules Consisting of Caffeic Acid Crosslinked with Terephthaloyl Chloride (TC)

600 mg of caffeic acid (Sigma) are dissolved in 6 ml of a buffer of pH 9.8. This solution is emulsified, by agitation at 5000 rpm, in 30 ml of cyclohexane to which 5% of Span 85® has been added. After 5 min, 40 ml of a 5% (w/v) solution of TC in a 1:4 (v/v) chloroform/cyclohexane mixture are added to the emulsion and agitation is maintained for 30 min. 40 ml of cyclohexane are then added to the reaction medium in order to stop the reaction.

After washing, a creamy-white sediment is obtained which is formed of microcapsules with a diameter of 2–10 µm, clear contents and a sharply defined wall. A white powder is obtained after lyophilization. Microscopic examination of the rehydrated powder shows intact spherical microcapsules.

EXAMPLE 27

Manufacture of Microcapsules Consisting of Phloroglucinol Crosslinked with Terephthaloyl Chloride The protocol described in Example 26 is applied using as the aqueous phase a solution containing 10% of phloroglucinol (Sigma) in the buffer of pH 11. This gives a white sediment formed of microcapsules with granular contents and a diameter of 2–10 µm.

EXAMPLE 28

Manufacture of Microcapsules Consisting of Protocatechuic Acid Crosslinked with Terephthaloyl Chloride The protocol described in Example 26 is applied using as the aqueous phase a solution containing 10% of protocatechuic acid (Sigma) in the buffer of pH 11. This gives a white sediment formed of microcapsules with clear contents and a diameter of 2–10 µm.

EXAMPLE 29

Manufacture of Microcapsules Consisting of DL-3, 4-di-hydroxyphenylalanine (DL-DOPA) Crosslinked with Terephthaloyl Chloride The protocol described in Example 26 is applied using as the aqueous phase a solution containing 10% of DL-DOPA (Sigma) in the buffer of pH 9.8. This gives a khaki-colored sediment formed of microcapsules with granular contents and a diameter of 2–10 µm.

EXAMPLE 30

Manufacture of Microcapsules Consisting of Curcumin Crosslinked with Terephthaloyl Chloride The protocol described in Example 26 is applied using as the aqueous phase a solution containing 10% of curcumin (Sigma) in 1M sodium hydroxide. This gives a bright yellow sediment formed of microcapsules with clear contents and a diameter of 2–10 μm.

EXAMPLE 31

Manufacture of Microcapsules Consisting of Ellagic Acid Crosslinked with Terephthaloyl Chloride The protocol described in Example 26 is applied using as the aqueous phase a solution containing 10% of ellagic acid (Sigma) in the buffer of pH 11. This gives a greenish-brown sediment formed of microcapsules with a diameter of 10–15 μm.

EXAMPLE 32

Manufacture of Microcapsules from Silymarin

The protocol described in Example 26 is applied using as the aqueous phase a solution containing 10% of silymarin (Silimarina /S, Indena) in 3M sodium hydroxide. This gives a light orange sediment formed of irregularly shaped microcapsules with a diameter of 2–8 μm.

EXAMPLE 33

Manufacture of Microcapsules from Rutin

The protocol described in Example 26 is applied using as the aqueous phase a solution containing 10% of rutin (trihydrate, Sigma) in 1M sodium hydroxide. This gives an orange sediment formed of spherical microcapsules with a diameter of 3–5 μm.

EXAMPLE 34

Manufacture of Microcapsules from a *Gingko biloba* Extract

The protocol described in Example 26 is applied using as the aqueous phase a solution containing 10% of dry *Gingko biloba* extract (Indena) in 3M sodium hydroxide. After dispersion in distilled water, a compact beige sediment of low bulk is obtained which is formed of irregularly shaped microcapsules with a mean diameter of 10.79 μm (determination with a Coulter LS 100® granulometer, Coultronics).

EXAMPLE 35

Manufacture of Microcapsules from a *Gingko biloba* Extract with the Addition of a Polyethylene Glycol The protocol described in Example 26 is applied using as the aqueous phase a solution containing 10% of dry *Gingko biloba* extract (Indena) in 3M sodium hydroxide containing 5% v/v of polyethylene glycol [PEG 200, Sigma]. After dispersion in distilled water, a bulky beige sediment is obtained which is formed of perfectly spherical microcapsules with a mean diameter of 27.94 μm (determination with a Coulter LS 100® granulometer, Coultronics).

This Example shows that the addition of a polyethylene glycol to the aqueous phase makes it possible to increase the hydrophilicity of the microcapsules.

EXAMPLE 36

Manufacture of Microcapsules from Grape Seed Procyanidolic Oligomers (GS PCO) Crosslinked with Sebacoyl Chloride and Containing an Oil An aqueous phase containing 15% of GS PCO (INDENA) in the buffer of pH 11 is prepared.

An oily phase is prepared by adding 0.3 ml of sebacoyl chloride to 6 ml of olive oil.

3 ml of the oily phase, used as the disperse phase, are emulsified in 10 ml of the aqueous phase by agitation at 5000 rpm.

The reaction is allowed to develop for 60 minutes.

The medium is diluted by the addition of 100 ml of distilled water. The microcapsules are then separated off and washed with water.

This gives a creamy-white supernatant formed of microcapsules with a diameter of 10–30 μm. Microscopic examination shows that each oil droplet is trapped in a membrane. Dispersed in water, the microcapsules are stable for at least 2 months in an oven at 45° C.: the microcapsules are intact and the water is colorless.

EXAMPLE 37

Demonstration of the Anti-free Radical Activity of the Microcapsules According to the Invention Different microcapsules according to the invention were tested for their capacity to scavenge free radicals.

The test used was the so-called "NBT" (nitroblue tetrazolium) test, the principle of which utilizes the reduction of NBT to a blue dye, namely formazan blue, by reaction with superoxide anions $O_2^-$ formed from the enzymatic hypoxanthine-xanthine oxidase system. Xanthine oxidase catalyzes the oxidation of hypoxanthine to xanthine and then to uric acid with the formation of superoxide anions. If the test compound introduced into the reaction medium possesses an anti-free radical activity, it will "scavenge" the superoxide anions, thereby reducing the formation of blue dye.

This test is well known to those skilled in the art and has been used and described especially by: DE LAMIRANDE E. et al., Fertility and sterility, 1993, 59 (6), 1291–5; RAMESH Chander et al., Biochemical Pharmacology, 1992, 44 (1), 180–183.

The formation of formazan blue is determined calorimetrically, for example by means of a UV-visible spectrophotometer at a wavelength of 560 nm.

The formation of this dye as a function of time is linear over the first five minutes. The reducing activity of the superoxide anion will therefore be expressed by the slope of the line obtained. Comparison of this slope with that of a control not containing a free radical "scavenger" will make it possible to establish the efficacy of the scavenging effect of the test product.

Procedure

1—Reagents:

[T]: TRIS-HCl buffer, 0.05M, pH 7.4 (TRIZMA PRE-SET pH crystals, SIGMA)

[N]: Nitroblue Tetrazolium, $10^{-3}$M (Grade III, SIGMA), prepared in [T]

[H]: Hypoxanthine, $0.5.10^{-2}$M, prepared in [T]

[X.O]: Xanthine Oxidase, 1.67 U/ml, prepared in [T]

The hypoxanthine and xanthine oxidase solutions are prepared for immediate use; the NBT solution can be stored for several days in a refrigerator at +4° C. in the dark.

2—Preparation of the samples:

The test products, i.e. the microcapsules of crosslinked plant polyphenols according to the invention, were dispersed in solution [T] at a concentration of 1 mg of product per ml of buffer. Thus the microcapsules used had either been lyophilized beforehand and were dispersed directly in the buffer solution, or were separated by centrifugation from a suspension freshly obtained by the processes described in the foregoing Examples.

As a comparative experiment, a solution of the same plant polyphenols but not crosslinked, at a concentration of 1 mg/ml in |T|, was also prepared.

3—Equipment:

The analyses were performed on a spectrophotometer of the UV-visible type connected to a recorder. The wavelength is set at 560 nm.

4—Implementation:

For each product analysis, three series of spectrophotometer cells are prepared from the above-described reagents and dispersions or solutions of test products. The contents of these cells are summarized in Table I below, in which the amounts of products or reagents are expressed in ml.

TABLE I

|  | REAGENTS (ml) | | | | |
| --- | --- | --- | --- | --- | --- |
|  | TEST | |T| | |N| | |H| | |E| |
| CELLS 0 | 0% | 2.4 | 0.1 | 0.5 | — |
| CELLS 1 | 100% | 2.3 | 0.1 | 0.5 | — |
| CELLS 2 | X | 2.2 | 0.1 | 0.5 | 0.1 |

[E]: sample to be studied

After homogenization, these solutions are equilibrated with the ambient air at 25°±1° C. for 20 min. After 20 min, each of these cells is subjected to a spectrophotometric recording for 5 min. Cell 0 is recorded directly.

The recording of cells 1 and 2 does not start until immediately after 0.1 ml of the xanthine oxidase solution has been added to the reaction medium.

More precisely, cells 2 will be recorded at a precise time, for example 2, 3, 4 or 5 min after introduction of the enzyme. Before the photometric reading is made, care will have been taken to remove the microcapsules from the solution contained in the cells, for example by centrifugation. It is therefore necessary, at the start of the experiment, to prepare a sufficient number of cells 2 to make the photometric readings at the different desired times.

The spectrophotometric recording of cells 0 gives the mean slope P0, which is very close to 0. That of cells 1 gives the mean slope P1 and represents 100%, i.e. the maximum effect of the superoxide anion $O_2-$. Finally, that of cells 2 gives the mean slope P2, which is intermediate between P0 and P1. This slope represents the inhibition due to the "scavenging effect" of the products analyzed.

The percentage inhibition "A" is given by the following equation:

$$A = \frac{(P1 - P0) - P2}{P1 - P0} \times 100$$

Three tests were performed for each analysis and gave rise to mean values. These mean values are all collated in Table II below.

TABLE II

| Test product Example no. | Non-cross-linked GS PGO | Ex. 1 | Ex. 3 | Ex. 5 | Ex. 6 | Ex. 9 | Ex. 11 | Ex. 15 |
| --- | --- | --- | --- | --- | --- | --- | --- | --- |
| Anti-free radical activity A% | 91 ± 2 | 81 ± 4 | 51 ± 1 | 71 ± 2 | 83 ± 1 | 79 ± 3 | 64 ± 5 | 78 ± 2 |

GS PCO = Grape Seed Procyanidolic Oligomer

Note:

All the microcapsules tested had been lyophilized beforehand with the exception of the microcapsules of Example 15, which had been separated by centrifugation from a freshly obtained suspension.

These results demonstrate that the crosslinked plant polyphenols according to the invention, in the form of microcapsules, surprisingly preserved an anti-free radical activity of substantially the same magnitude.

Thus the microcapsules according to the invention preserved the activity of the plant polyphenols from which they originated and can advantageously be used for this purpose in different compositions, especially cosmetic or pharmaceutical compositions, while at the same time exhibiting a very high stability.

Various formulations of cosmetic or pharmaceutical compositions, especially dermatological compositions, are given below.

EXAMPLE 38

Base Composition for Cosmetic or Pharmaceutical Composition

Lyophilized microcapsules of crosslinked PCO, as obtained according to any one of the preceding Examples 1 to 8, 15 or 16, are dispersed at a concentration of 0.1% in a greasy excipient, for example a greasy excipient available commercially under the tradename "natural cold cream" from Laboratoires Roche Posay. It is found that the microcapsules disperse very readily in the excipient and give a preparation of homogeneous appearance with a very slight tinge of pink.

This composition is particularly stable.

EXAMPLE 39

Composition in the Form of a Protective Gel

This composition has the following ingredients in percentages by weight:

|  | % by weight |
| --- | --- |
| Water | 64.30 |
| Imidazolineurea preservative | 0.20 |
| Carbomer 940 ® | 0.50 |
| 10% sodium hydroxide | 1.90 |
| 96° alcohol | 20.08 |
| 0.7% suspension of microcapsules of grape seed procyanidolic oligomers according to Example 15 | 14.30 |
|  | 100.00 |

Preparative procedure:

The first step is to prepare the Carbomer 940 gel in conventional manner by dissolving the preservative in water and then dispersing the Carbomer 940. This is followed by neutralization with the sodium hydroxide solution, with stirring. The alcohol is added and, finally, the suspension of microcapsules is added, with stirring, to give a composition in the form of a gel.

This gel is applied to the skin, for example on the face or hands, and then enables a cream and/or a make-up to be applied.

EXAMPLE 40

Cosmetic Composition in the Form of a Day Cream

This composition is composed of the following three phases A, B and C:

|  | % by weight |
| --- | --- |
| Phase A | |
| Steareth 2 | 0.8 |
| Steareth 21 | 2.2 |
| Cetyl palmitate | 1.5 |
| Stearyl alcohol | 1.8 |
| Glyceryl monostearate | 1.5 |
| Caprylic capric triglyceride | 4.6 |
| Stearic acid | 2.6 |
| Perhydrosqualene | 11.0 |
| Parabens | 0.5 |
| Phase B | |
| Water | 57.20 |
| Methylparaben | 0.15 |
| Carbomer 940 | 0.20 |
| Phase C | |
| Water | 1.26 |
| Sodium hydroxide | 0.14 |
| Phase D | |
| 0.7% suspension of microcapsules of grape seed procyanidolic oligomers (GS PCO) according to Example 15 | 14.3 |
| Phase E | |
| Perfume | 0.25 |
|  | 100.00 |

Preparative procedure:

The greasy phase (phase A) is prepared in conventional manner by mixing the ingredients indicated above, after which the mixture is heated to 85° C.

The aqueous phase (phase B) is then prepared in the following manner:
- the water is heated to 85° C. and the preservative is dissolved therein,
- the Carbomer 940 is then dispersed and the temperature is maintained at 85° C.

The aqueous phase B is poured slowly into the greasy phase A in an agitating mixer of the YSTRAL® type. Agitation is continued while allowing the mixture to cool. When the temperature reaches 70° C., the mixture is neutralized with the phase C (sodium hydroxide solution). The suspension of microcapsules of GS PCO (phase D) is then added at 40° C. Agitation is still continued while allowing the mixture to cool, and perfume is added at 35° C. (phase E). Agitation is continued until the oil-in-water emulsion obtained reaches room temperature.

The stability of this cream was determined. When kept in an oven at 40° C., it underwent no color modification after one month, in contrast to a control sample of cream prepared from the phases A, B, C and E and containing non-crosslinked PCO, exposed to the same conditions.

A day cream is thus obtained which can be applied regularly to the skin, for example on the face or hands.

What is claimed is:

1. Microcapsules comprising a wall formed of at least one plant polyphenol interfacially crosslinked with a diacid halide crosslinking agent.

2. Microcapsules according to claim 1 further comprising a protein, a polysaccharide, a polyalkylene glycol or a mixture thereof.

3. Microcapsules according to claim 2 wherein the wall comprises a protein, a polysaccharide, a polyalkylene glycol or mixture thereof co-crosslinked with the at least one plant polyphenol.

4. Microcapsules according to claim 2 wherein the protein possesses a specific enzymatic activity, the activity adding to activity inherent in the at least one plant polyphenol.

5. Microcapsules according to claim 1 wherein the at least one plant polyphenol is a monocyclic or polycyclic plant polyphenol selected from the group consisting of flavonoids, isoflavonoids, neoflavonoids, gallotannins, ellagotannins, catechol, DL-3,4-dihydroxyphenylalaline, catecholamines, phloroglucinol, phenolic acids, phenolic esters, phenolic heterosides, curcumin, polyhydroxylated coumarins, polyhydroxylated lignans or neolignans, and mixtures thereof.

6. Microcapsules according to claim 5 wherein the flavonoids are selected from the group consisting of a flavone, a flavonol, a flavone or flavonol heteroside, a flavanone, a flavanone heteroside, diosmoside, a biflavonoid, a flavone or flavonone dimer, a chalcone, a flavanonol, a flavan-3-ol, a polymer formed of flavan-3-ol basic structural units, a proanthocyanidin, an anthocyanoside, and mixtures thereof.

7. Microcapsules according to claim 6 wherein the flavonoids are selected from the group consisting of mixtures of citroflavonoids extracted from various Citrus (Rutaceae), a mixture of flavonoids extracted from Silybum marianum (Compositae), or silymarin, extracts of Gingko biloba (Gingkoaceae), anthocyanoside-rich extracts of blueberry, blackcurrant fruits, grape skins or red vine leaf, fruit juices, red wines, and mixtures thereof.

8. Microcapsules according to claim 2 wherein the proteins are selected from the group consisting of albumins, globulins, fibrinogen, casein, vegetable proteins, glutelins, degraded glutelins, solubilized scleroproteins, collagen, atelocollagen, gelatin, gelatin hydrolyzates, peptones, hemoglobin, enzymes, mixtures containing hydrophilic proteins, milk, whey proteins, soya flour and mixtures of atelocollagen and glycosaminoglycans.

9. Microcapsules according to claim 2 wherein the polysaccharide is selected from the group consisting of dextrans, alginic acid and water-soluble salts thereof, vegetable gums, carrageenans, pectins, soluble starch, soluble cellulose and glycosaminoglycans.

10. Microcapsules according to claim 2 wherein the polyalkylene glycol is selected from the group consisting of polyethylene glycols and polypropylene glycols.

11. Microcapsules according to claim 1 prepared by the interfacial crosslinking of an emulsion having an aqueous phase containing from 1% to 40% by weight of plant polyphenols, based on total weight of the aqueous phase and optionally containing proteins, polysaccharides, polyalkylene glycols or mixtures thereof, in a total concentration in the aqueous phase between 0.1 and 30% by weight based on total weight of the aqueous phase.

12. Microcapsules according to claim 1 additionally comprising at least one water-soluble, liposoluble or insoluble active substance in the form of a solution, suspension or emulsion.

13. Microcapsules according to claim 12 wherein the active substance incorporated in the microcapsules is selected from the group consisting of a mineral substance which reflects solar radiation, a vegetable oil, a deodorized fish liver oil, or an oily solution of a liposoluble substance, an essential fatty acid, a ceramide, a liposoluble ascorbic acid derivative, or a liposoluble sun filter, a photoactive substance and mixtures thereof.

14. Microcapsules according to claim 1 having a diameter of between 0.1 μm and 3 mm.

15. A process for the manufacture of microcapsules, comprising the steps of:

a) preparing an aqueous phase which contains at least one plant polyphenol, b) preparing a hydrophobic phase which optionally contains at least one surfactant, c) emulsifying said aqueous phase in the hydrophobic phase to form an emulsion in which the hydrophobic phase forms a continuous phase and the aqueous phase forms a dispersed phase, d) adding a diacid halide crosslinking agent, dissolved in a liquid miscible with the hydrophobic phase to the emulsion, with agitation, in order to effect interfacial crosslinking of the crosslinking agent and the plant polyphenol contained in the aqueous phase, e) maintaining the agitation for a reaction time sufficient to allow crosslinking resulting in the formation of microcapsules having walls comprising the at least one plant polyphenol crosslinked by the crosslinking agent, and f) collecting the microcapsules formed.

16. A process for the manufacture of microcapsules, comprising the steps of:

a) preparing a hydrophobic phase in which a diacid halide crosslinking agent is dissolved, b) preparing an aqueous phase which contains at least one plant polyphenol and optionally, at least one surfactant, c) emulsifying the hydrophobic phase in the aqueous phase to form an emulsion in which the aqueous phase forms a continuous phase and the hydrophobic phase forms a dispersed phase, d) agitating the emulsion for a reaction time sufficient to allow crosslinking resulting in the formation of microcapsules having walls comprising the at least one plant polyphenol crosslinked by the crosslinking agent, and e) collecting the microcapsules formed.

17. A process according to claim 15 or 16 further comprising adding a protein, a polysaccharide, a polyalkylene glycol or a mixture thereof to the aqueous phase during the preparation thereof.

18. A process according to claim 15 or 16 additionally comprising washing the microcapsules formed to remove excess crosslinking agent and the at least one plant polyphenol which has not crosslinked or is not encapsulated in the microcapsules.

19. A process according to claim 15 or 16 additionally comprising lyophilizing the microcapsules.

20. A process according to claim 15 or 16 wherein the diacid halide is an aliphatic or aromatic diacid chloride.

21. A process according to claim 15 or 16 wherein the diacid halide is present in a concentration of between 0.2% and 10% by weight of the aqueous and hydrophobic phases.

22. A process according to claim 15 or 16 wherein the crosslinking is conducted at a pH of between 8 and 14 maintained with a buffer solution or a solution of an alkaline agent.

23. A process according to claim 15 or 16 wherein the hydrophobic phase is produced from a hydrophobic liquid substance selected from the group consisting of halogenated and non-halogenated hydrocarbons, fatty acid esters, vegetable oils, and mixtures thereof.

24. A process according to claim 15 or 16 further comprising adding at least one active substance, in the form of a solution, suspension or emulsion, into the dispersed phase which is encapsulated.

25. A cosmetic, pharmaceutical, dermatological, dietetic or food composition, comprising microcapsules as defined in claim 1.

26. A composition according to claim 25 having a concentration of said microcapsules of between 0.01 and 10% by weight.

27. A composition according to claim 25 wherein the microcapsules are fresh.

28. A composition according to claim 25 wherein the microcapsules are in a dehydrated form.

29. A composition according to claim 25 for preventing ageing of the skin.

30. A cosmetic method of treating a human in order to prevent actinic ageing of the skin due to free radicals, comprising applying to areas of skin or hair sensitive to action of free radicals a composition comprising an effective amount of microcapsules with a wall of diacid halide crosslinked plant polyphenols, and a cosmetically or pharmaceutically acceptable excipient, vehicle or carrier.

31. A cosmetic method of treatment according to claim 30 wherein the microcapsules are present in the composition in a concentration of between 0.01 and 10% by weight.

32. A process for the preparation of a composition incorporating one or more plant polyphenols, comprising, in order to prevent any impairment, or any color modification of the composition over time, while at the same time preserving the activity of the plant polyphenols, said polyphenols are incorporated into said composition in the form of microcapsules comprising a wall formed of at least one plant polyphenol interfacially crosslinked with a diacid halide crosslinking agent.

33. A process according to claim 32 wherein the composition is selected from the group consisting of a cosmetic composition, a pharmaceutical composition, a dermatological composition, a dietetic composition and a food composition.

34. A process according to claim 32 wherein the activity preserved is an anti-free radical activity, an antioxidizing activity or both.

35. Microcapsules according to claim 1, wherein the at least one plant polyphenol is a plant extract, tincture, fruit juice or wine.

* * * * *